(12) United States Patent
Marra et al.

(10) Patent No.: US 10,524,702 B2
(45) Date of Patent: Jan. 7, 2020

(54) SYSTEM AND METHOD OF MONITORING PATIENTS IN HOSPITAL BEDS

(71) Applicants: Sociedade Beneficente Israelita Brasileira Hospital Albert Einstein, São Paulo (BR); I-HealthSys Produtos Médicos Ltda—ME, São Carlos (BR)

(72) Inventors: Alexandre Rodrigues Marra, Sao Paulo (BR); Oscar Fernando Pavao Dos Santos, Sao Paulo (BR); Marcelo Prado, Sao Carlos (BR); Renaldo Massini Junior, Sao Carlos (BR); Guilherme Machado Gagliardi, Sao Carlos (BR); Felipe Kermentz Ferraz Costa, Sao Carlos (BR); Tales Roberto De Souza Santini, Muzambinho (BR); Alvaro Costa Neto, Sao Carlos (BR)

(73) Assignees: Sociedade Beneficente Israelita Brasileira Hospital Albert Einstein, São Paulo (BR); I-HealthSys Produtos Médicos Ltda—ME, São Carlos (BR)

( * ) Notice: Subject to any disclaimer, the term of this patent is extended or adjusted under 35 U.S.C. 154(b) by 397 days.

(21) Appl. No.: 15/450,423

(22) Filed: Mar. 6, 2017

(65) Prior Publication Data
US 2018/0049677 A1 Feb. 22, 2018

(30) Foreign Application Priority Data
Aug. 16, 2016 (BR) .............................. 102016018876

(51) Int. Cl.
*A61B 5/11* (2006.01)
*A61B 5/00* (2006.01)
(Continued)

(52) U.S. Cl.
CPC .......... *A61B 5/1128* (2013.01); *A61B 5/0075* (2013.01); *A61B 5/0077* (2013.01);
(Continued)

(58) Field of Classification Search
CPC ..... A61B 5/1128; A61B 5/746; A61B 5/0077; A61B 5/7278; A61B 5/1077;
(Continued)

(56) References Cited

U.S. PATENT DOCUMENTS 8,073,535 B2 * 12/2011 Jung .................... A61B 5/01
340/501
9,104,789 B2 * 8/2015 Gross .................... G16H 40/63
(Continued)

OTHER PUBLICATIONS

Tamura, T., T. Togawa, and M. Murata. "A bed temperature monitoring system for assessing body movement during sleep." clinical physics and physiological measurement 9.2 (1988): 139. (Year: 1988).*

*Primary Examiner* — Bobbak Safaipour
(74) *Attorney, Agent, or Firm* — Patterson + Sheridan, LLP

(57) ABSTRACT

The present invention discloses a system of monitoring patients in hospital beds, the system comprising: at least one image capture element (2) disposed in a hospital bed (10) and configured to generate an image parameter (11) of a patient (12) disposed in the hospital bed (10). The system further comprises at least one processor, configured to generate a temperature map (13) of the patient (12) from the image parameter (11). Also disclosed is a method (40) of monitoring patients in hospital beds.

11 Claims, 14 Drawing Sheets

(51) Int. Cl.
    *A61B 5/01*         (2006.01)
    *A61B 5/107*       (2006.01)

(52) U.S. Cl.
    CPC ............ *A61B 5/015* (2013.01); *A61B 5/1077* (2013.01); *A61B 5/1079* (2013.01); *A61B 5/1115* (2013.01); *A61B 5/7278* (2013.01); *A61B 5/746* (2013.01); *A61B 2576/00* (2013.01)

(58) Field of Classification Search
    CPC ..... A61B 5/1115; A61B 5/015; A61B 5/0075; A61B 5/1079; A61B 2576/00
    See application file for complete search history.

(56) References Cited

U.S. PATENT DOCUMENTS

| | | | |
|---|---|---|---|
| 2008/0021344 A1* | 1/2008 | Jung | A61B 5/00 600/549 |
| 2008/0031512 A1* | 2/2008 | Mundermann | G06K 9/00342 382/154 |
| 2008/0077020 A1* | 3/2008 | Young | A61B 5/0205 600/484 |
| 2010/0264228 A1* | 10/2010 | Jung | A61B 5/00 236/94 |
| 2015/0109442 A1* | 4/2015 | Derenne | G06F 16/78 348/143 |
| 2018/0247427 A1* | 8/2018 | Geiger | G06K 9/00201 |

* cited by examiner

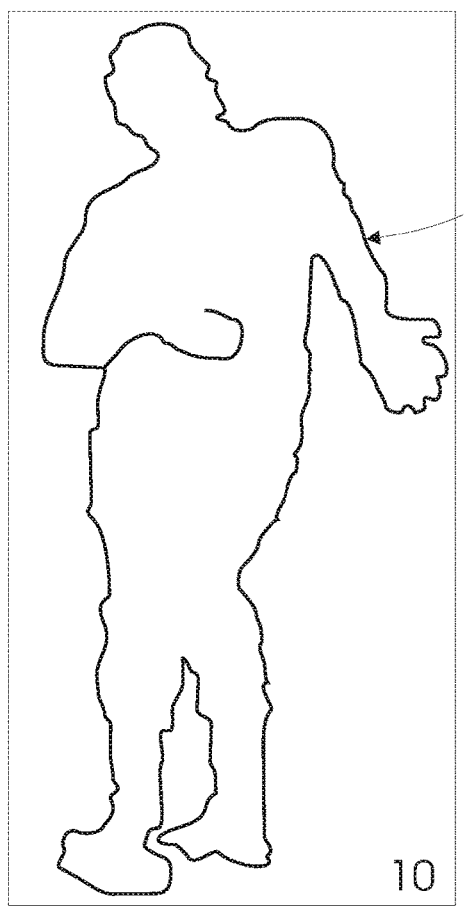 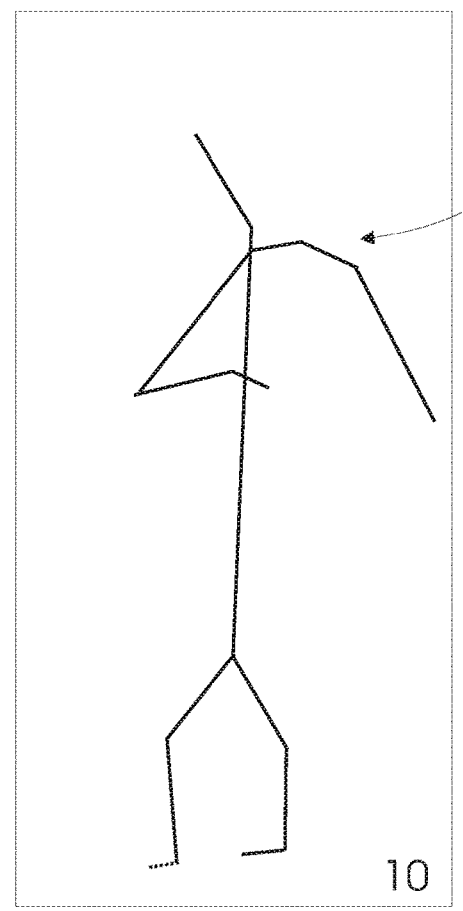
FIG. 3 (a)                    FIG. 3 (b)

| | | | |
|---|---|---|---|
| Xxxxxxxxxxxxxx xxxxxx xxx   18 | | 304 | |
| A | 36.6 °C | H | 37.3 °C |
| B | 37.0 °C | I | 38.1 °C |
| C | 37.3 °C | J | 38.2 °C |
| D | 37.3 °C | K | 38.0 °C |
| E | 37.3 °C | L | 37.3 °C |
| F | 37.3 °C | M | 37.3 °C |
| G | 37.3 °C | N | 37.3 °C  16 |

FIG.8

SYSTEM AND METHOD OF MONITORING PATIENTS IN HOSPITAL BEDS

The present invention relates to a system of monitoring patients in hospital beds, more specifically, to a system capable of determining the patient's movement in the bed, as well as the temperature of his or her body and specific regions thereof. In accordance with the proposed system, the present invention further relates to a method of monitoring patients in hospital beds.

DESCRIPTION OF THE PRIOR ART

Monitoring of patient temperature in hospital beds, such as Intensive Care Units (ICUs), is very important for monitoring the patient's condition.

Temperatures quite above a patient's normal conditions may indicate infectious processes, reactions to medications given, reactions inherent in the patient's own disease, or due to the patient's post-surgical procedures or chemotherapy procedure that the patient received.

In some cases, excessive patient temperatures (e.g. above 40 degrees Celsius) can lead to death if the patient remains in this state of high body temperature for too long a time.

Yet, it is important to monitor temperatures in specific regions of the patient's body. For example, in regions where surgical interventions were performed, where it was necessary to cut the patient's tissue for a certain procedure, such as tumor withdrawals, organ transplants or other procedures where access to certain internal organs was necessary.

In such cases, following the surgical procedure and suturing of the region where tissue opening for internal access was carried out, it is important to monitor the patient's region or limb for follow-up of possible infectious processes due to the healing process of the suture region or to infectious processes of transplanted organs.

In addition to monitoring the patient's temperature, it is also necessary to supervise patient's movement, since excessive movement in critically-ill patients, for example, due to neurological interventions or due to tumors in regions of the brain or due to pathologies that provoke sudden or compulsive movements may endanger the health of the patient himself.

Moreover, the patient in compulsive movement may cause damage to himself due to invasive devices that may have been placed on the patient, such as intravenous medication, bladder catheters, in which compulsive movements may cause withdrawal of such devices abruptly.

Furthermore, due to a sudden movement of the patient the invasive devices may be contaminated due to their disconnection with the patient and subsequent contact with the patient's own hand or whoever is around them, for example, a health professional or escort, such that in order to hold the patient during the compulsive movement he may have touched the invasive device without having performed the proper hygiene.

Yet, involuntary disconnection of invasive devices may cease medication or disconnect monitoring equipment that has been placed on the patient, such as electrocardiogram, pressure or other monitoring equipment.

In some cases, the patient in a compulsive state may fall from the bed and cause injuries to the head or other limbs, putting the patient's own health at risk and worsening his state of health, and in some extreme cases may cause death.

Thus, it is of the utmost importance that monitoring the temperature and movement of the patient are properly performed, thus ensuring his full recovery and treatment.

The prior art discloses some documents which are intended to monitor the patient in a hospital bed, such as patent application US 2015/0141838.

Although disclosing the possibility of monitoring the patient temperature and movement, this US document has the drawback of using two sensors connected to the bed of the patient.

This fact directly associates the bed to the sensor, that is, to use the system proposed in this document, a specific bed must be used, so that in some types of bed, monitoring may not occur or occur in an inefficient manner.

Further, the evaluation of the patient movement in US 2015/0141838 is based on the centroid of the patient's representation; such way of evaluation is not efficient for detecting movements in specific regions of the body.

For example, from the calculation and determination of the centroid, it is not possible to effectively evaluate the specific movement of the arm, leg or torso of the patient, as well as to perform a comparison between the movement of these segments.

The system proposed in the present invention evaluates the patient's movement through the representation of the silhouette image and segmentation of the patient's body into various modules (segments), such as head, trunk, arm, forearm, hand, thigh, leg and foot.

Thus, one can not only evaluate the movement (and temperature) of each of these segments specifically, as well as store the measurement history for each segment.

OBJECTS OF THE INVENTION

The present invention relates to the provision of a patient monitoring system in hospital beds able to monitor the temperature of the patient's body as well as specific regions of this patient.

The present invention relates to the provision of a patient monitoring system in hospital beds able to monitor the movement of the patient's body as well as specific regions of this patient.

A further object of the present invention resides in a system, as mentioned above, configured to represent the patient's body in several segments (such as head, trunk, arm, forearm, hand, thigh, leg and foot) and able to monitor the temperature and movement of these segments.

The present invention further aims at a system configured to provide parameters of the patient's temperature and movement in real time to a remote station, such a remote station able to receive the parameters of at least one hospital bed.

A further object of the present invention is to provide a system configured to display, within the hospital bed, data regarding the patient's temperature and movement, as well as the history of the analyzes performed.

Furthermore, the present invention relates to the provision of a system capable of monitoring a plurality of hospital beds arranged in different locations.

In addition, the present invention objects to provide a system able to alert the medical professional that the evaluation of the patient's temperature and movement exceeded the values and parameters considered as acceptable.

Finally, the present invention relates to a method for monitoring patients in hospital beds according to the proposed system.

BRIEF DESCRIPTION OF THE INVENTION

Disclosed is patient monitoring system in hospital beds, the system comprising: at least one image capture element disposed in a hospital bed and configured to generate an image parameter of a patient disposed in the hospital bed. The system further comprises at least one processor, configured to generate a patient temperature map from the image parameter.

Also disclosed is a method for monitoring patients in hospital beds, the hospital bed comprising at least one image capture element, so that the image capture element is associated with a processor, the method comprising the steps of: generating an image parameter of a patient disposed in the hospital bed; thus generating a patient temperature map from the generated image parameter.

BRIEF DESCRIPTION OF THE DRAWINGS

The present invention will be further described in more detail based on one example of realization represented in the drawings. The figures show:

FIG. 2(a) illustrates the image parameter generated by the image capture element and FIG. 2(b) illustrates the temperature map generated from the image parameter;

FIG. 3—is a further representation of the patient disposed in the hospital bed, wherein FIG. 3(a) illustrates a contour of the patient and FIG. 3(b) is a representation of the patient's segmented model;

FIG. 8—is a preferred illustration of the representation of the temperature parameters specific to each segment of the segmented model;

DETAILED DESCRIPTION OF THE FIGURES

Figure 1:
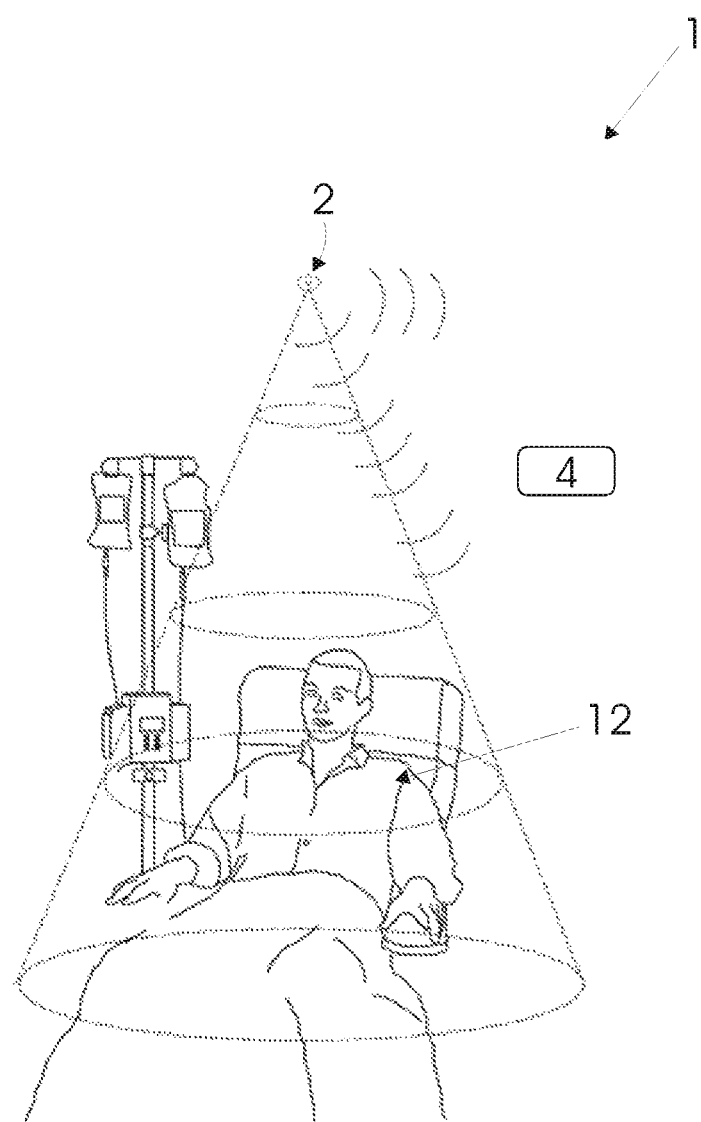
FIG. 1—is a representation of a hospital room provided with the system proposed in the present invention.

The present invention discloses a system for monitoring patients in hospital beds 1, also referenced only as system 1.

Basically, the proposed system 1 monitors the temperature and movement of a patient 12 in a hospital bed 10 through the detection of infrared electromagnetic waves.

Hospital bed 10 is to be understood as the location in which the patient 12 accommodates in a room of a health facility, for example, in an Intensive Care Unit (ICU), the bed in which the patient 12 is accommodated.

Alternatively, hospital bed 10 may be understood as an armchair disposed in the room of the health unit and used by the patient in some situations, for example, resting or feeding.

It is emphasized that the term hospital bed 10 does not necessarily refer to a hospital, so that any health facility, such as clinics, offices, nursing homes and care units should be understood as having hospital beds 10.

In general terms, and for a better understanding of the invention, the hospital bed 10 should be understood as any place, in a health facility, or treatment unit, or follow-up unit, where the patient can accommodate for long or short periods of time.

A preferred embodiment of the system 1 for monitoring patients in hospital beds is illustrated in FIGS. 1 to 15 and preferably refers to a hospital bed 10 of an Intensive Care Unit.

As can be seen from FIG. 1, the system 1 comprises at least one image capture element 2 disposed in a hospital bed 10.

Preferably, the image capture element 2 is configured as an electromagnetic wave detection sensor at the infrared wavelength or a camera for infrared wave detection.

From the detection of the electromagnetic waves emitted by the body of the patient 12, the system 1 will monitor, as best described below, the temperature and movements performed by the patient.

Still referring to FIG. 1, the system 1 preferably comprises a display 4 disposed next to the hospital bed 10 and configured so as to display the temperature parameters 16 and movement 17 of the patient 12, i.e. the display 4 is configured in order to display data related to the temperature and the movement of the patient 12.

Preferably, the association between the image capture element 2 and the display 4 occurs via radiofrequency (RF); thus, it becomes necessary that such components comprise suitable RF modules for said communication to occur.

Preferably, the image capture element 2 should be disposed above the hospital bed 10, for example, on the ceiling of the room of the intensive treatment unit where the bed 10 is disposed. In a preferred embodiment, it may comprise an internal thermometer for calibrating the bed reference temperature, i.e., calibrating the image capture element 2 with the ambient temperature of the bed in which the patient 12 is disposed. It is highlighted that any other temperature calibration means known in the state of the art could be used.

Still more preferably, each room of the ICU must have an image capture element 2, so that if the system 1 is to be used in rooms comprising more than one hospital bed 10, it is preferable to use a sensor 2 arranged above each bed 10.

In order to detect the patient's temperature 16 and movement 17 parameters, the sensor 2 must capture an image (image parameter 11) of the patient 12 and, from a processor, such an image parameter 11 will be transformed into a temperature map 13 of patient 12.

Figure 2:
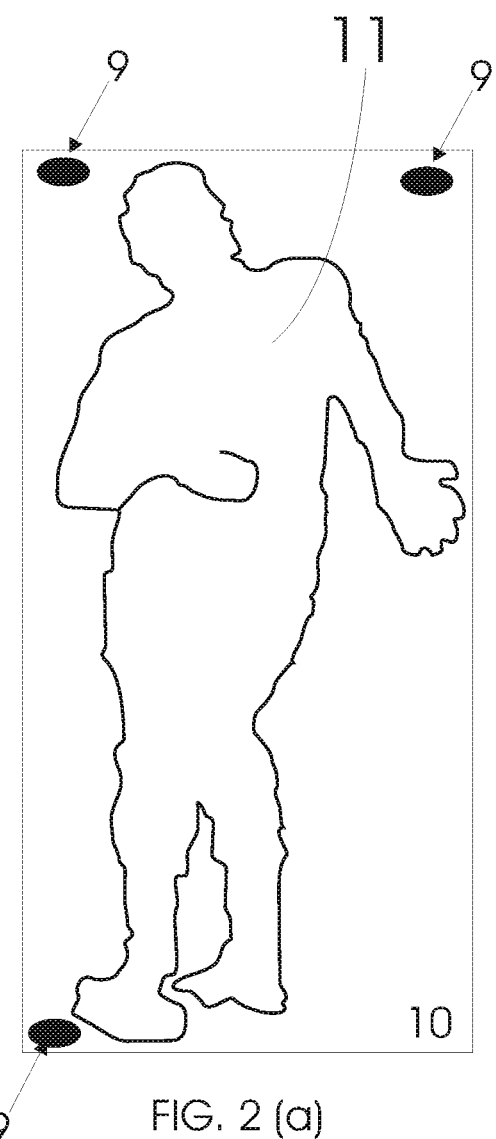
FIG. 2—is a representation of the patient disposed in the hospital bed, where
Figure 2:
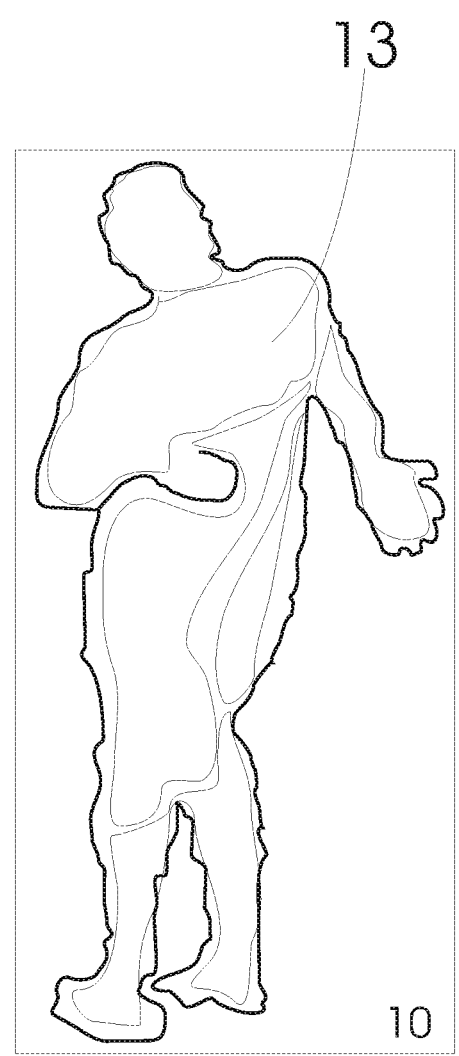

Referring to FIG. 2, FIG. 2(a) illustrates the image parameter 11 generated by the image capture element 2 and FIG. 2(b) illustrates the temperature map 13 generated from the image parameter.

The temperature map 13 discloses to the health professional a representation, preferably by means of colors, of the patient's body temperature. Preferably, an indication through red, yellow and blue colors may be represented, thereby indicating regions with higher, average and lower temperatures, respectively.

The temperature range associated with each color representation can be set by the user of the proposed system 1.

Still from the image parameter 11, the proposed system 1 generates, through the processor, a contour 14 of such a parameter 11 and also a segmented model 15 of the body of the patient 12.

The contour 14 of the image parameter is illustrated in FIG. 3(a), which shows an approximate representation of the silhouette (profile) of the body of the patient 12 generated from the image (image parameter 11) captured by sensor 2.

FIG. 3(b) is a representation of the segmented model 15 generated by the system 1 proposed in the present invention and through the processor contained therein. Said segmented model 15 represents a vector illustration of the body of the patient 12 and indicates certain regions (20, 22, 24, 26) of this patient.

Figure 4:
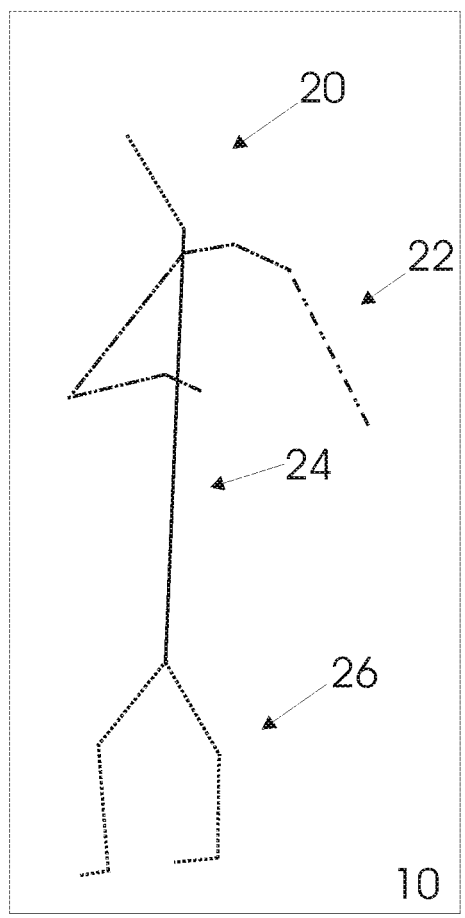
FIG. 4—is a representation of the segmented model indicating the regions of the patient's body.

For example, with reference to FIG. 4, the segmented model 15 allows the representation of the region relative to the head 20, the upper member 22, the trunk 24 and the leg 26 of the patient 12.

Figure 5:
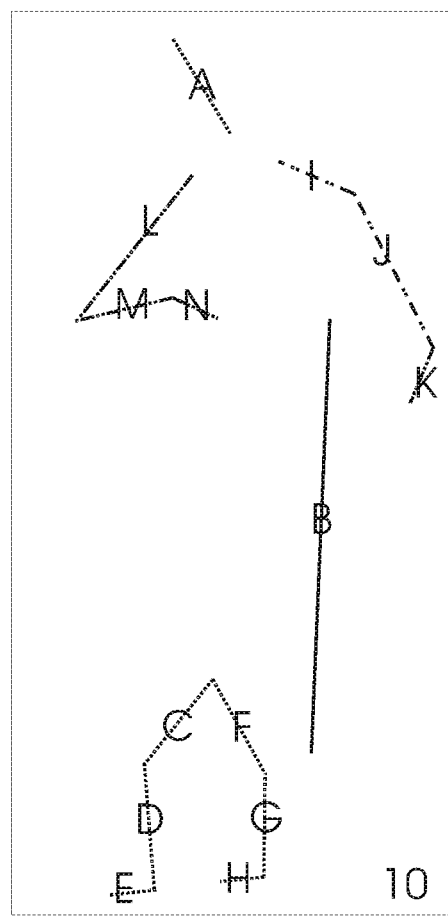
FIG. 5—is a further representation of the segmented model indicating each of the plurality of segments comprising thereof.

Thus, each of regions 20, 22, 24 and 26 of patient 12 corresponds to at least one segment of the segmented model, as shown in FIG. 5.

In this regard, and with reference to FIG. 5, each region can be represented by only one segment or by a plurality of segments of the segmented model 15.

For example, the portion relating to the head 20 of the patient 12 comprises the segment A and the trunk 24 comprises the segment B. The region relative to the patient leg 26 comprises segments C, D, E, F, G, H. Finally, and yet referring to FIG. 5, the region relating to the upper member 22 of the patient 12 comprises the segments I, J, K, L, M and N.

This way, in regions comprising more than one segment, for example the upper member 22 and legs 26, each segment may represent a more specific portion of this region.

Thus, in reference to the region relating to the patient's leg 26, segment C represents the right thigh, segment D represents the region between the patient's knee/right shin and finally segment E represents the the patient's right foot. Similarly, segments F, G and H represent the same specific regions of the patient's left leg.

Thus, for the region relating to the upper member 22 of patient 12, segments I, J and K represent specific regions of the patient's upper left limb, such as arm, forearm and hand, respectively. Similarly, segments L, M and N represent the same regions of the patient's right upper limb 22.

Figure 6:
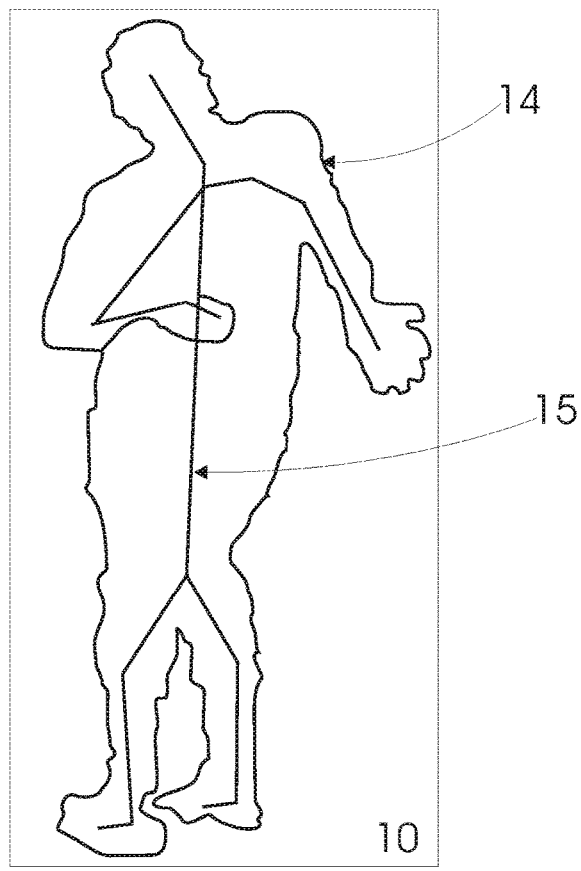
FIG. 6—is a representation of the overlapping of the segmented model to the contour of the patient.

For a better representation of the location of each segment A, B, C, D, E, F, G, H, I, J, K, L, M and N of the segmented model 15, such model 15 should, preferably, be overlapped with the representation of the patient's contour 14. Thus, such representation will enable the medical professional to better and more clearly reproduce the location of each segment relative to the complete image of the body of the patient 12. Such overlapping, realized by the processor of system 1, is illustrated in FIG. 6.

The segmentation of the body of the patient 12 by means of the segmented model 15 and the plurality of segments A, B, C, D, E, F, G, H, I, J, K, L, M and N allows that the specific temperature of each of these segments be informed to the health care professional.

Thus, if patient 12 has undergone a surgical intervention in the brain, the health care professional can monitor the specific temperature of segment A.

Such monitoring can be performed remotely, for example, the temperature parameters 16 of segment A (or any other segment) can be sent to a central monitoring station of the hospital, where data from each hospital room will be displayed on at least one screen.

Alternatively, the temperature parameters 16 may be sent to the health care professional's cell phone (or any other personal electronic device), and the health care professional may, regardless of where he is located, monitor the temperature of segment A.

Further, the temperature parameters 16 may be constantly displayed on the display 4 in the health unit room; thus, any health care professional who comes to medicate/visit the patient 12 may have access to the temperature parameters 16.

Obviously, predefined alarms, if the value of the temperature parameter 16 exceeds a limit (upper/lower) considered as acceptable (limits defined by the physician for each segment of the segmented model 15) may be programmed by the health care professional, thus, said professional will receive a notification either in his cell phone, either in the monitoring center of the hospital or on the display 4.

Moreover, previously measured temperature parameters 16 must be stored by the system 1, thus enabling the health care professional to consult the history of the temperature parameters 16 of a given patient 12. Such a consultation may be performed either in the physician's cell phone, either on display 4 or in the monitoring center of the hospital.

FIG. 8 is a preferred illustration of the representation of the temperature parameters 16 (temperature values) specific to each segment of segments A, B, C, D, E, F, G, H, I, J, K, L, M and N. As already mentioned, such a representation can occur on display 4, as well as in the monitoring center of the hospital or in the cell phone of the health care professional.

Preferably, and for better health care professional's control, it is proposed that basic information of patient 18 (name, reason for hospitalization) and also the number of his/her room (in this case, room 304) be displayed along with the temperature parameters 16.

Thus, due to the representation of the temperature 16 in each of the segments A, B, C, D, E, F, G, H, I, J, K, L, M, and N, the health care professional can quickly visualize which portion of the patient's body (segment) is at a temperature above the normal one.

For example, by evaluating the representation of FIG. 8, the professional will quickly notice that the I, J and K segments (left arm, forearm, and hand) are above an acceptable temperature. Thus, he will be able to take the necessary measures.

Preferably, a visual indication, for example in red, for segments I, J and K, can be represented, thus highlighting that these regions of the body have a temperature above acceptable.

Further, the health care professional may, through representation preferably in the control unit of the hospital or in his or her cell phone, have a representation regarding the temperature parameters 16 of all patients 12 of a given floor or of all patients 12 under the care of a particular physician.

Figure 9:
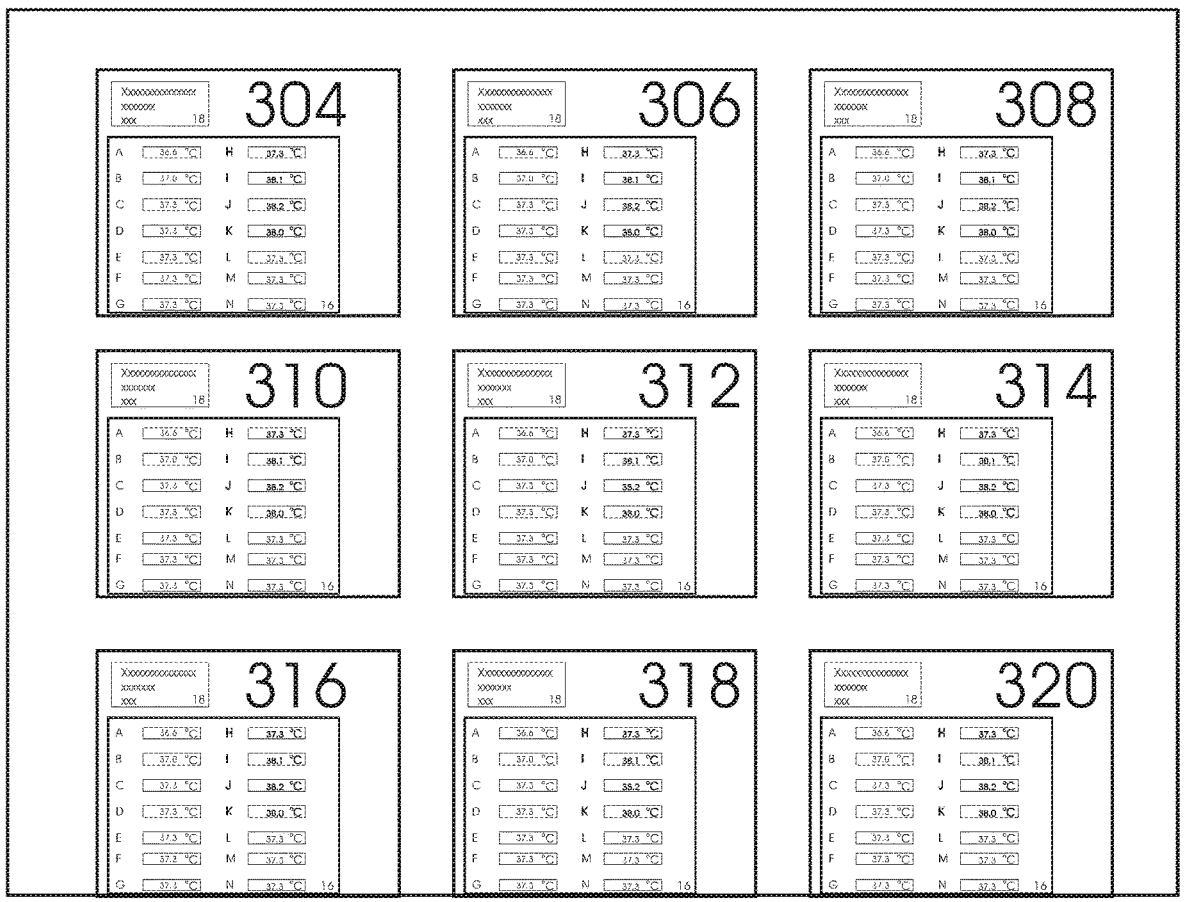
FIG. 9—is a preferred illustration of the representation of the temperature parameters of all patients on a specific floor of a hospital unit.

Such a representation is illustrated in FIG. 9, in which the indication of each patient is shown, with its respective room number (304 to 320) and the temperature parameters 16 of each of them.

In addition, the system 1 proposed in the present invention is configured so as to generate the segmented model 15 of the patient at subsequent instants of time, for example, every 10 seconds, or at time intervals previously set by the health care professional.

In a preferred embodiment, the time interval defined by the health care professional for generation of the segmented model 15 is valid for all patients 12 under monitoring, i.e., for this preferred embodiment of the present invention, the segmented model 15 would be generated in subsequent time intervals and for patients 12 of beds 10 of number 304 to 320.

Alternatively, the health care professional could define specific time intervals for each bed 10 of interest, for example, if in the hospital bed number 316 there is a patient 12 requiring more specific monitoring, the physician may define a time interval, for example, from 1 second to generation of the segmented model 15, while the other 10 beds would generate the segmented model for every 10 seconds.

Obviously, by generation of the segmented model 15 at subsequent time instants, there should also be understood as the generation of each of the plurality of segments A, B, C, D, E, F, G, H, I, J, K, L, M and N, also at different time instants, and consequent generation of temperature parameters 16 for each instant.

In this preferred embodiment of the present invention, and so that the proposed objects be achieved, the segmented model 15 of patient 12 should preferably be generated every 0.03 second.

This fact enables that system 1, proposed in the present invention, and more specifically its processor, be further configured to generate at least one movement parameter 17 of the patient 12.

By movement parameter 17, it should be understood that the system 1 is able to monitor the movement of the patient 12 in the hospital bed 10, thus evaluating the occurrence, for example, of jerky, compulsive movements, bed falls, convulsions, movement caused by bacteremia, respiratory disruption (apnea), or any movement performed by patient 12 in bed 10.

In order to generate the movement parameter 17 of patient 12, a midpoint $M_A$, $M_B$, $M_C$, $M_D$, $M_E$, $M_F$, $M_G$, $M_H$, $M_I$, $M_J$, $M_K$, $M_L$, $M_M$ and $M_N$ of each segment A, B, C, D, E, F, G, H, I, J, K, L, M and N of the segmented model 15 should be determined.

In other words, for each segmented model 15 generated at subsequent time instants, midpoint M of each segment must be determined.

Figure 10:
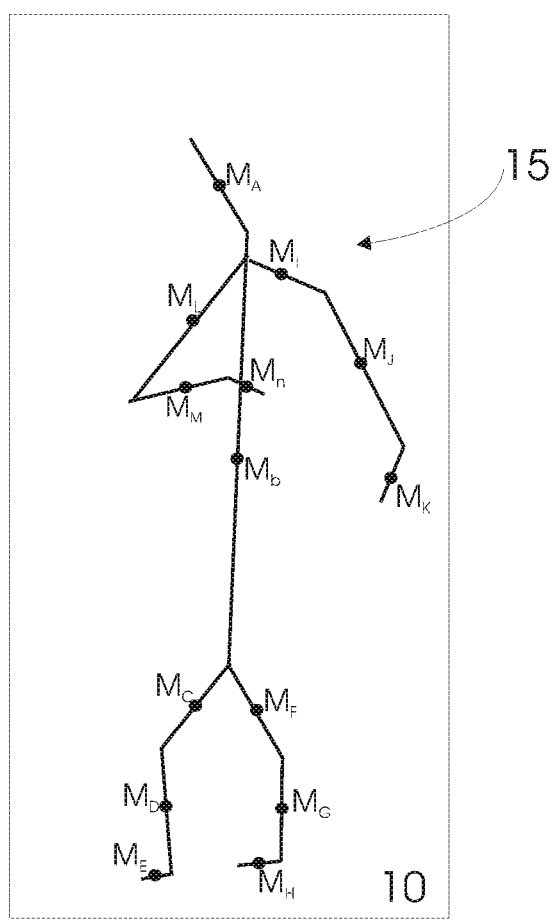
FIG. 10—is a representation of the segmented model illustrating the midpoint arrangement of each segment of the plurality of segments.

FIG. 10 shows a representation of the segmented model 15 of patient 12 wherein midpoint M of each segment is determined, thus one has midpoints $M_A$, $M_B$, $M_C$, $M_D$, $M_E$, $M_F$, $M_G$, $M_H$, $M_I$, $M_J$, $M_K$, $M_L$, $M_M$, $M_N$.

Once the position of each of the midpoints is determined, their orientation should also be determined.

To this end, this preferred embodiment of the system 1 proposed in the present invention is based on a global coordinate system in conjunction with a local coordinate system of the patient 12.

Figure 11:
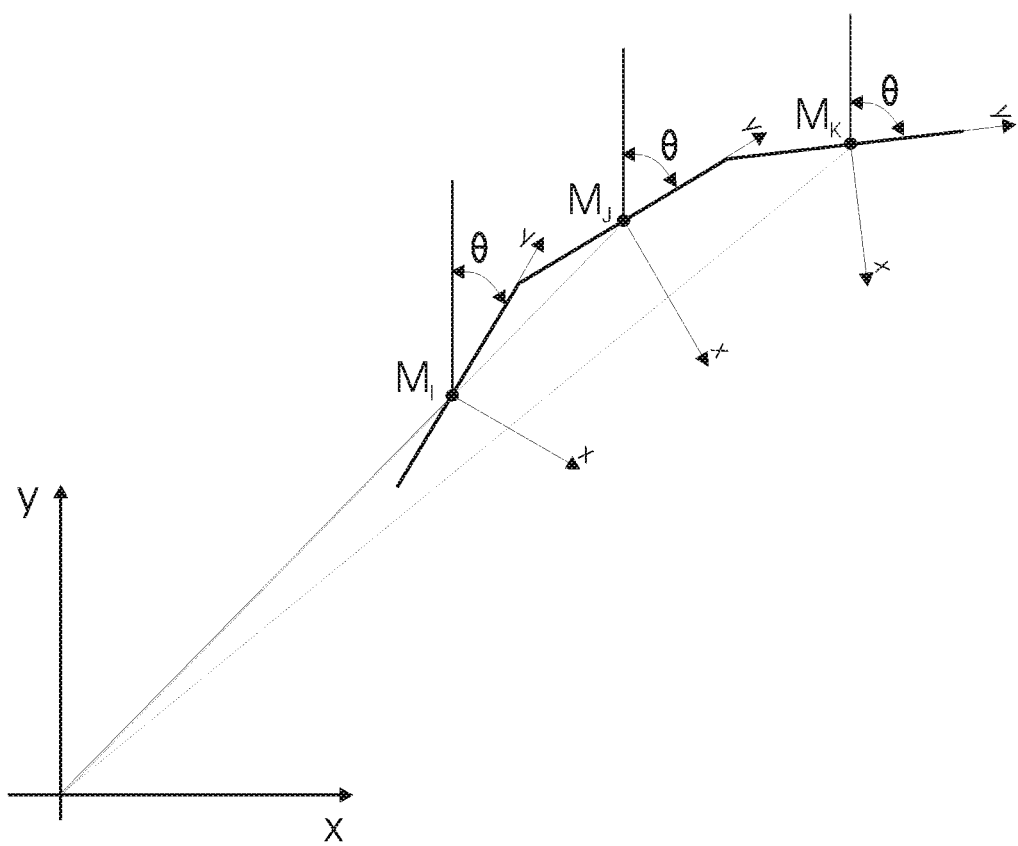
FIG. 11—is a representation of the global coordinate system and the local coordinate system used to generate the patient's movement parameters.

Referring to FIG. 11, the local coordinate system is to be understood as the cartesian coordinate system x and y for each midpoint M, in this preferred representation, of midpoints $M_I$, $M_J$ and $M_K$.

The global coordinate system is to be understood as the reference x and y coordinate system for all average points, i.e., as seen from FIG. 11, each of the midpoints $M_I$, $M_J$ and $M_K$ converge to the global coordinate system.

More specifically, FIG. 11 is a representation of how the orientation of the midpoints M of the segmented model 15 is determined. It is pointed out that such a figure represents, for a better understanding of the invention, only the segments I, J and K and their respective midpoints, so that, of course, the description performed is valid for all other segments of the segmented model 15.

Figure 12:
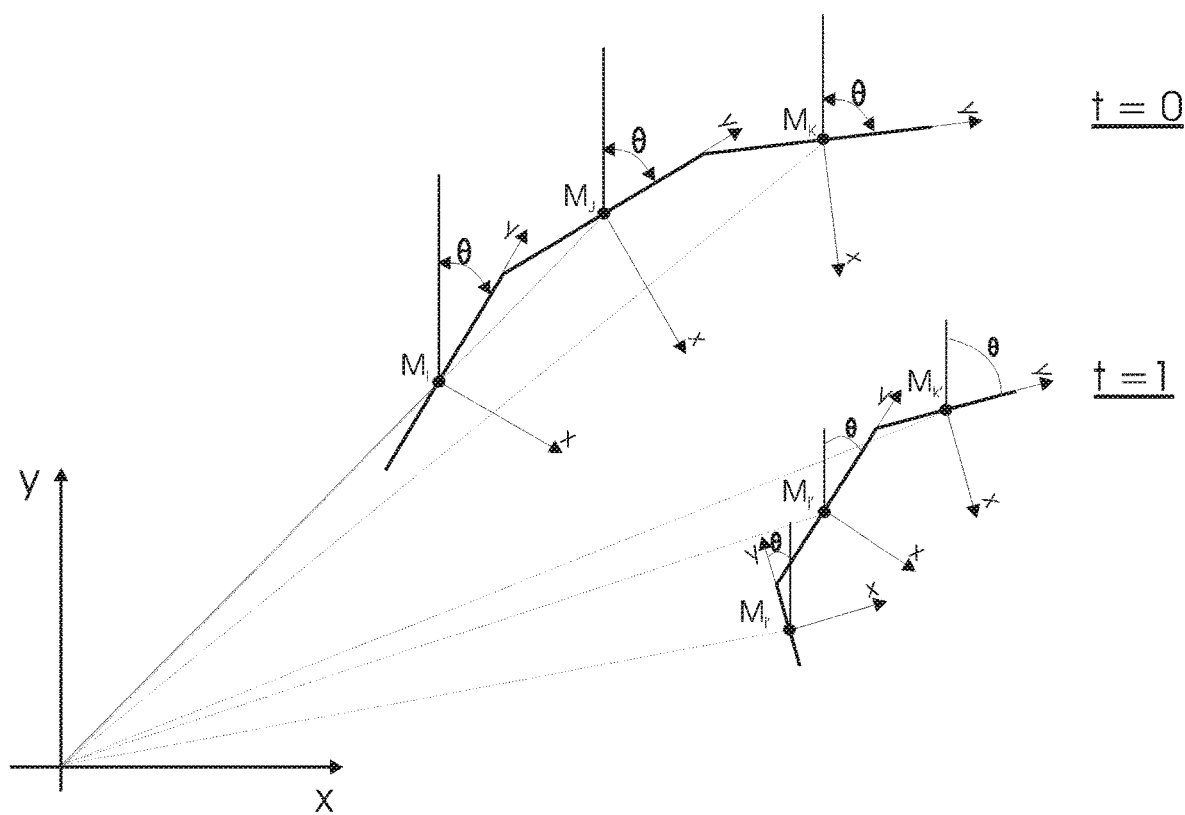
FIG. 12—is an additional representation of the global coordinate system and the local coordinate system.

Thus, for each time instant, the position and orientation of each midpoint is determined. Referring to FIG. 12, one can see the determination of the position and orientation of midpoints $M_I$, $M_J$ e $M_K$ in a first time instant, referenced as t=0, and the determination of midpoints $M_{I'}$, $M_{J'}$ and $M_{K'}$ of the same segments at a later time instant, referenced as t=1.

Thus, for each measured time instant, certain patient movement parameters 17 will be generated. More specifically, the movement parameters 17 are generated on the basis of the kinematic calculation of the position and orientation of the midpoints of each segment.

In this way, with reference to FIG. 12 and considering the time instants t=0 and t=1, the movement parameters 17 will be generated based on the kinematic calculation between the midpoints $M_I$, $M_J$ e $M_K$ e $M_1$, $M_{J'}$ and $M_{K''}$.

More specifically, for each time instant, the following movement parameters 17 are generated: Segment translational distance 30, segment translational speed 31, segment translation acceleration 32, translation angle 33 (Θ) of each segment, angular speed 34 of each segment, angular acceleration 35 of each segment, linear displacement 36 of each segment and angular displacement 37 of each segment.

Figure 13:
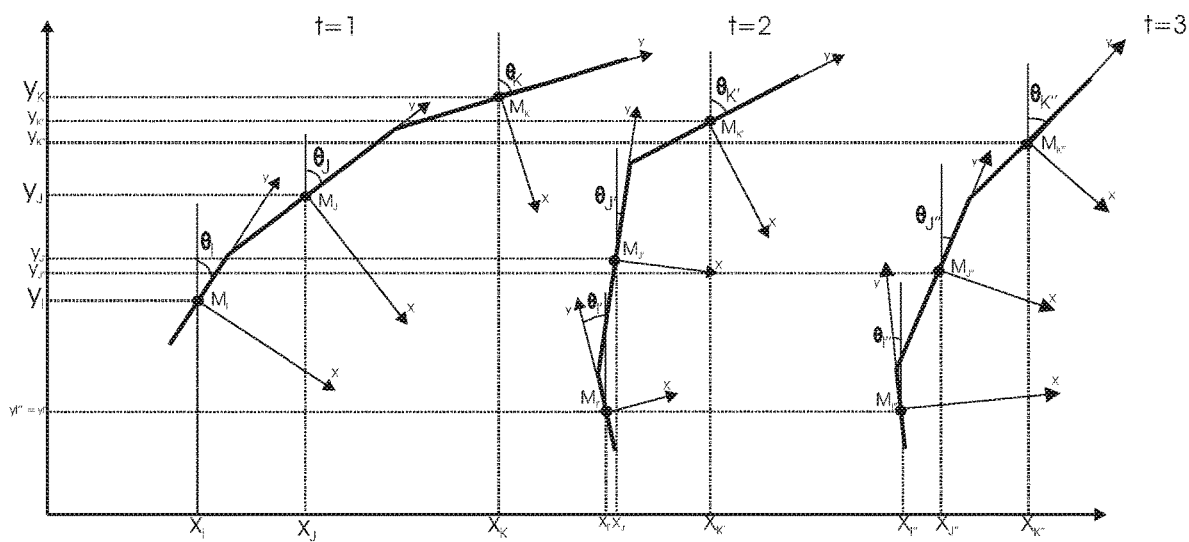
FIG. 13—is a representation of the determination of the patient's movement parameters.

The generation and calculation of these movement parameters 17 occur based on the determination of the coordinates of the local coordinate system with reference in the global coordinate system, as shown in FIGS. 11, 12 and 13.

More specifically, FIG. 13 allows a better visualization in relation to the determination of the movement parameters 17 by considering the position of segments I, J and K and their respective midpoints $M_I$, $M_J$ and $M_K$ in three distinct positions, each one of these representing a time instant (t=1, t=2 and t=3).

Referring to FIG. 13, the movement parameter 17 referring to the displacement 36 of each segment can be determined by the coordinates of each midpoint $M_I$, $M_J$ and $M_K$ at each of the time instants.

For example, for the displacement 36 occurring between t=1 and t=2, one has:

$$D_{x(I)}=x_{I'}-x_I; D_{x(J)}=x_{J'}-x_J; D_{x(K)}=x_{K'}-x_K; e\ D_{y(I)}=y_{I'}-y_I;$$

$$D_{y(J)}=y_{J'}-y_J; D_{y(K)}=y_{K'}-y_K.$$

Where $D_{x(I)}$, $D_{x(J)}$ and $D_{x(K)}$ are to be understood as the displacement on the x-axis of each of the midpoints of the segments I, J and K, respectively. Similarly, $D_{y(I)}$, $D_{y(J)}$ and $D_{y(K)}$ refer to the displacement on the y-axis of the midpoints of each of segments I, J and K, respectively.

Thus, one can also determine the translation speed 31 of each of the segments I, J and K as the ratio between the displacement and the period of time comprised between t=2 and t=1. Thus, the speed in the direction of the x and y axes at time t=2 is obtained by:

$$Speed_{x(I)2} = \frac{x_{I'} - X_I}{t_2 - t_1}; Speed_{x(J)2} = \frac{x_{J'} - X_J}{t_2 - t_1}; Speed_{x(K)2} = \frac{x_{K'} - X_K}{t_2 - t_1}$$

$$Speed_{y(I)2} = \frac{y_{I'} - y_I}{t_2 - t_1}; Speed_{y(J)2} = \frac{y_{J'} - y_J}{t_2 - t_1}; Speed_{y(K)2} = \frac{y_{K'} - y_K}{t_2 - t_1}$$

Thus, one can determine the movement parameter 17 relative to the translation distance of the segment 30 between the midpoints $M_I$, $M_J$ e $M_K$ and $M_{I'}$, $M_{J'}$ and $M_{K'}$ between time instants t=1 and t=2:

$$D_{MI',MI} = \sqrt{(X_{I'}-X_I)2+(Y_{I'}-Y_I)2}$$

$$D_{MJ',MJ} = \sqrt{(X_{J'}-X_J)2+(Y_{J'}-Y_J)2}$$

$$D_{MK',MK} = \sqrt{(X_{K'}-X_K)2+(Y_{K'}-Y_K)2}$$

Preferably, it is also possible to calculate movement parameters 17 relative to the angular displacement 37 of the segments I, J and K and their respective midpoints $M_I$, $M_J$ and $M_K$ between times t=2 and t=1. Thus, considering the angle of translation as Θ, one can obtain the angular displacement 37 ($Θ_{I',I}$, $Θ_{J',J}$ e $Θ_{K',K}$) between the instants t=1 and t=2 for the segments I, J and K. Reference is made to FIG. 13:

$$θ_{I',I}=θ_{I'}-θ_I; θ_{J',J}=θ_{J'}-θ_J; θ_{K',K}=θ_{K'}-θ_K;$$

Movement parameter 17 for the angular speed 34 of each of the segments I, J and K is determined by the ratio between the angular displacement ($Θ_{I',I}$, $Θ_{J',J}$ e $Θ_{K',K}$) and the time period between t=1 and t=2. Thus, by assigning $V_Θ$ the angular speed, one has:

$$V_{θI',I} = \frac{θ_{I'} - θ_I}{t_2 - t_1}; V_{θJ',J} = \frac{θ_{J'} - θ_J}{t_2 - t_1}; V_{θK',K} = \frac{θ_{K'} - θ_K}{t_2 - t_1}$$

In order to determine the movement parameter 17 relative to the translation acceleration 32, one can consider the translation speed 31 at one of the time instants (t=1, t=2 or t=3) as the initial speed and the translation speed 31 at a later time instant as the final speed.

Thus, one can determine the acceleration 32, for example, of segment I between instants t=2 and t=3 in the direction of the x-axis as being:

$$a_{x(I)} = \frac{Speed_{x(I)3} - Speed_{x(I)1}}{t_3 - t_2},$$

$$\text{wherein: } Speed_{x(I)3} = \frac{x_{I''} - x_{I'}}{t_3 - t_2} \text{ and } Speed_{x(I)1} = \frac{x_{I'} - x_I}{t_2 - t_1},$$

Equivalently, one can determine the acceleration in the direction of the x-axis for the segments J and K, as well as the acceleration in the direction of the y-axis for the segments I, J and K.

Also, one can determine the movement parameter 17 relative to the angular acceleration 35 ($a_Θ$), for example, between the instants t=2 and t=3 for the segment I:

$$a_{θ(I)3} = \frac{V_{θ(I)3} - V_{θ(I)1}}{t_3 - t_2}, \text{ wherein: } V_{θ(I)3} = \frac{x_{I''} - X_{I'}}{t_3 - t_2}, \text{ and } V_{θ(I)1} = \frac{x_{I'} - X_I}{t_2 - t_1}$$

Obviously, the angular acceleration 35 can be calculated for the other segments shown in FIG. 13, as well as one can calculate any of the movement parameters 17 for any of the segments A, B, C, D, E, F, G, H, I, J, K, L, M and N of the generated segmented model 15.

For a better understanding, it is understood that system 1 is able to calculate any movement parameter 17 from the kinematic calculation of the midpoints $M_A$, $M_B$, $M_C$, $M_D$, $M_E$, $M_F$, $M_G$, $M_H$, $M_I$, $M_J$, $M_K$, $M_L$, $M_M$, $M_N$ of the segmented model 15.

Accordingly, the health care professional will be indicated at least one of the movement parameters 17 of each segment of the segmented model 15.

Figure 14:
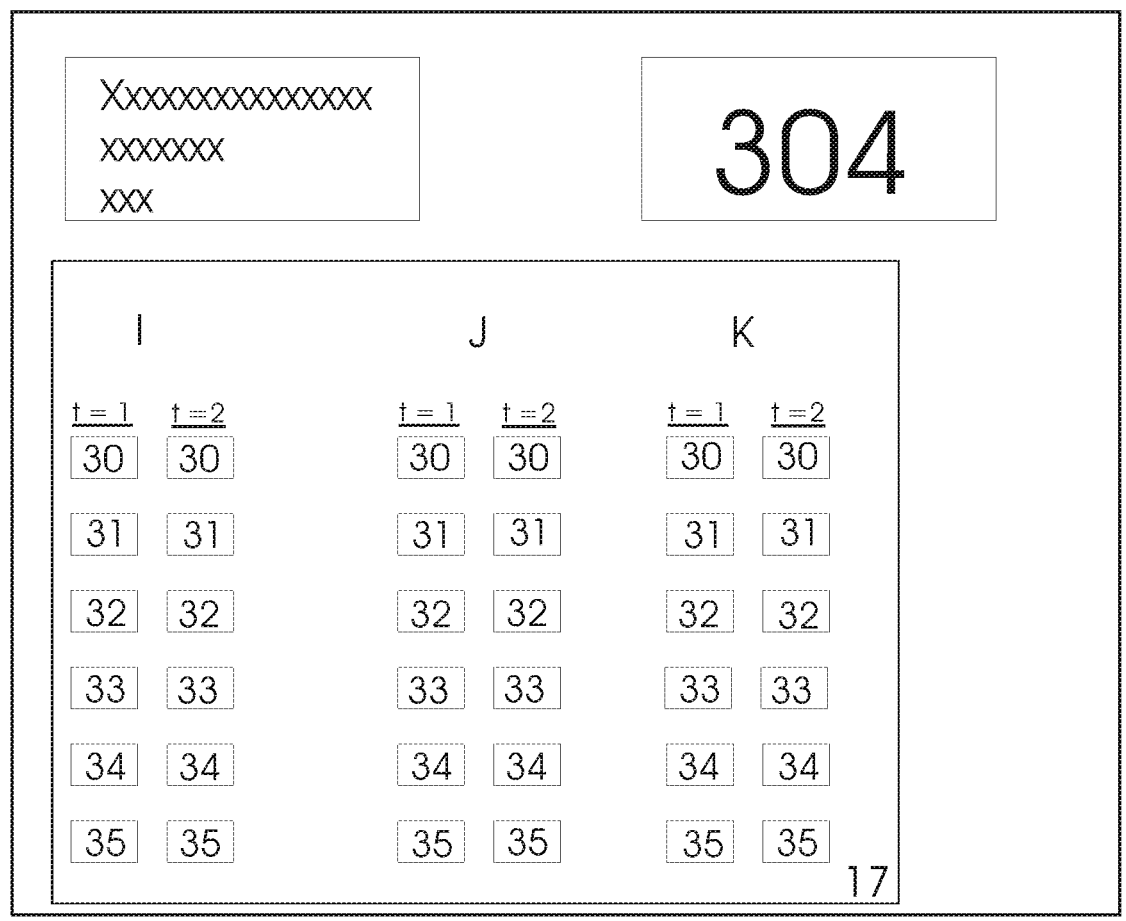
FIG. 14—is a preferred representation of the illustration of the patient's movement parameters.

For example, by considering the preferred representation of FIG. 13 as a representation of the segments I, J and K of the left arm of the patient 12, the health care professional will have a preferred indication, as shown in FIG. 14, of the movement parameters 17 at instant t=1 and at the later instant, t=2.

Thus, the representation of FIG. 14 will allow the health care professional to know the values, be absolute, or be in a comparison between the values generated at different time instants, referring to the patient's movement parameters 17, as translation distances 30, translation speed 31, translation acceleration 32, translation angle 33, angular speed 34 and angular acceleration 35.

Consequently, the representation of the movement parameters 17 may indicate that the patient is in convulsion if, for example, the parameters of translation speed 31, translation distance 30 and linear displacement 36 are above predefined limits.

It is further noted that reference to translation speed 31 may be used to determine, for example, the occurrence of tremors in the patient. The occurrence of tremors in relevant amplitudes (distance, spacing) may indicate that the patient is in convulsion.

Preferably, the user of the patient monitoring system in hospital beds 1 may assign predefined values for movement parameters 17 which indicate the occurrence, for example, of tremors in the patient or even convulsion.

For a better visualization of the health care professional regarding patient movement, the system 1 proposed in the present invention, through its processor, is configured so as to show the physician the segmented model 15 of the patient at subsequent time instants, such a representation referenced as a movement map 27.

In this way, the physician will have a clearer representation of the position of the patient 12, and of the movement thereof, as compared to the representation shown in FIG. 14.

Figure 15:
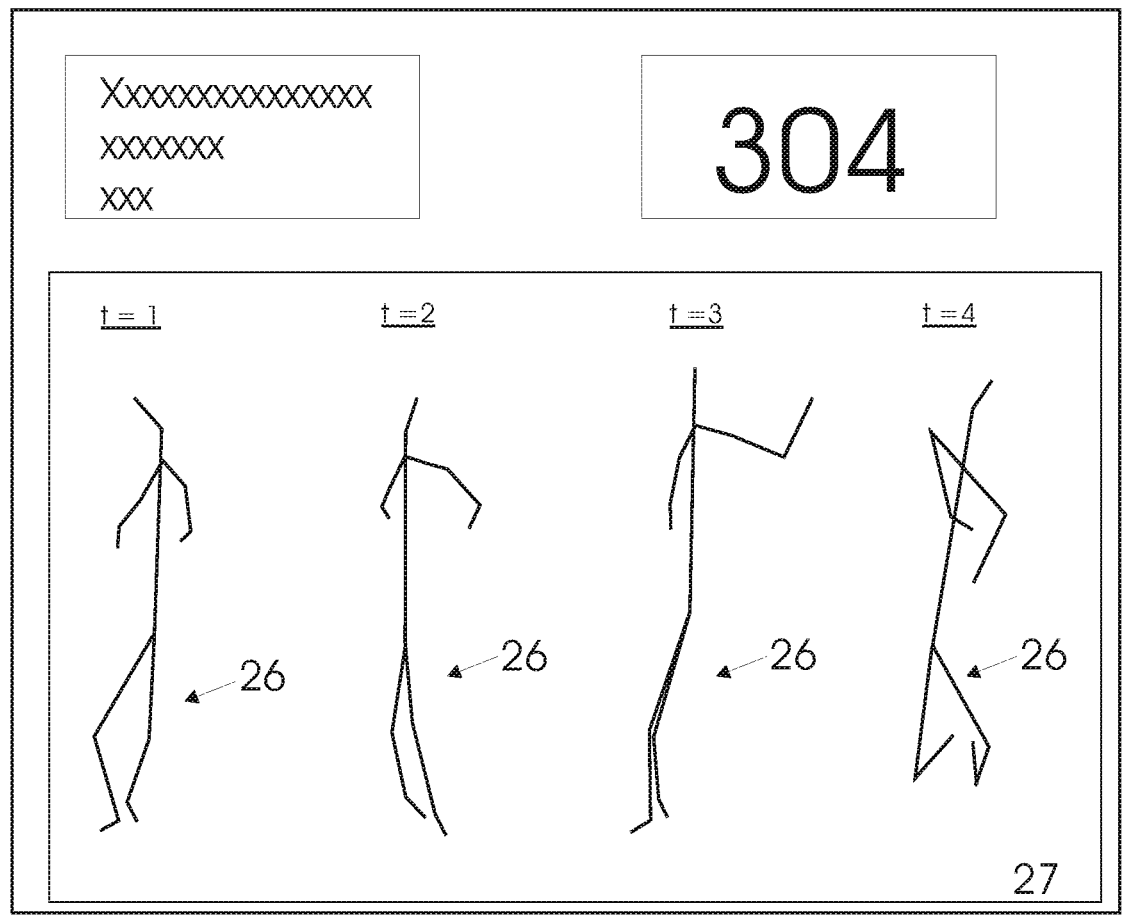
FIG. 15—is a preferred representation of the movement map generated with the patient's segmented models.

For example, and referring to FIG. 15, this figure shows the movement map 27 related to the segmented model 15 generated at subsequent time instants, for example, at instants t=1, t=2, t=3 et=4.

Thus, the physician can clearly observe a movement of the patient when comparing the instants t=1 and t=4, more specifically, and considering the preferred representation of FIG. 15, a contraction of the legs 26 of the patient 12 is observed.

Preferably, the time instants for generating the movement map 27 should be defined by the health care professional. Considering that this preferred embodiment of the present invention generates the segmented model 15 of the patient every 0.03 seconds, it is advised that the movement map 27 be generated in time intervals greater than that value, for example, every two seconds.

Thus, it is understood that the movement map 27 will be generated with the generated segmented models 15, for example, at time t=1 equivalent to the initial instant, t=2 equaling 2 seconds after the initial instant, t=3 equaling 4 seconds after the initial instant and t=4 equaling 6 seconds after the initial instant.

In this way, and in a preferred manner, over time the movement map 27 is updated so as to illustrate to the user (physician) of system 1, the movement map 27 with the last four segmented models generated.

In addition, the health care professional can select the time instants from each generated segmented model 15, for example, the health care professional may request system 1 to generate the movement map 27 with the models 15 generated at 2:00 p.m., 2:05 p.m., and 2:08 p.m. of a given day, times that preceded a patient-related event (surgery, death, among others).

Preferably, the movement parameters 17 and the movement map 27 can be displayed either in the cellular phone of the health care professional or in the hospital monitoring center or in the display 4 arranged in the hospital bed.

The system 1 proposed in the present invention is further able to determine a possible fall of the patient 12 from the hospital bed 10. To this end, at least one device 9 must be arranged at a known distance from the bed 10.

Said device 9 is preferably configured as an LED operating in the infrared spectrum, thus it emits known wavelength electromagnetic waves (infrared), thereby enabling determining the contours of the bed in which the patient 10 is disposed, as well as a possible fall of the patient from such a bed 10. Said device 9 is still used for determining the coordinate system shown in FIGS. 11, 12 and 13.

It is emphasized that the device 9 must operate at frequencies that do not match the frequency emitted by the patient's body, in order thereby to avoid that the patient is taken as reference instead of its bed 10. Also, the use of three devices 9 for correct determination of the limits of the bed 10 of the patient.

Figure 7:
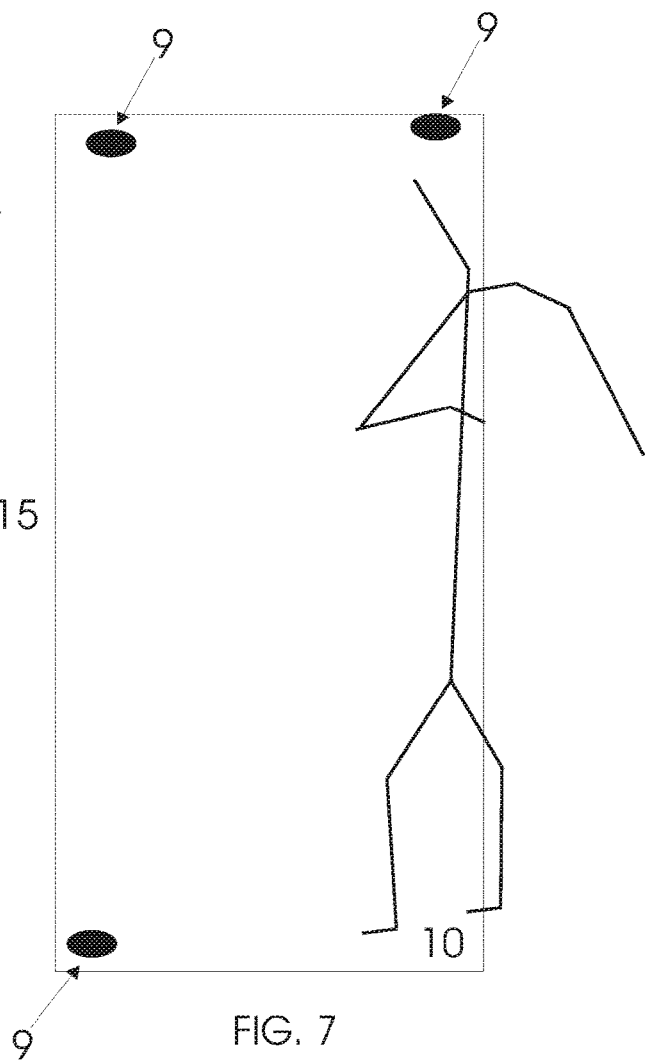
FIG. 7—is a representation of the segmented model disposed outside the boundaries of the hospital bed.

More specifically, the fall of patient 12 will occur if the segmented model 15 is generated outside the contours of the bed, for example, as shown in FIG. 7 of the present invention.

Obviously and as already described above, alarms can be predefined if the values of the parameters of temperature 16 and parameters of movement 17 exceed predetermined thresholds (min/max).

Such alarms can be specifically defined, for example, by considering each segment of the segmented model 15. Thus, if the patient has undergone a surgical intervention, or any other type of event, the health care professional can monitor such region (segment) with greater emphasis.

These thresholds of temperature and movement must be defined by the user of system 1, that is, the health care professional. In a preferred configuration, such thresholds may be altered either locally (within hospital bed 10) through the display 4, or in the hospital control unit, or may be remotely altered, e.g. via the cell phone of the health care professional.

Regardless of the setting location, it is advised that a password for access to system 1 by its user (s) be created.

In accordance with the system of monitoring patients in hospital beds 1 previously described, the present invention also relates to a method of monitoring patients in hospital beds.

Figure 16:
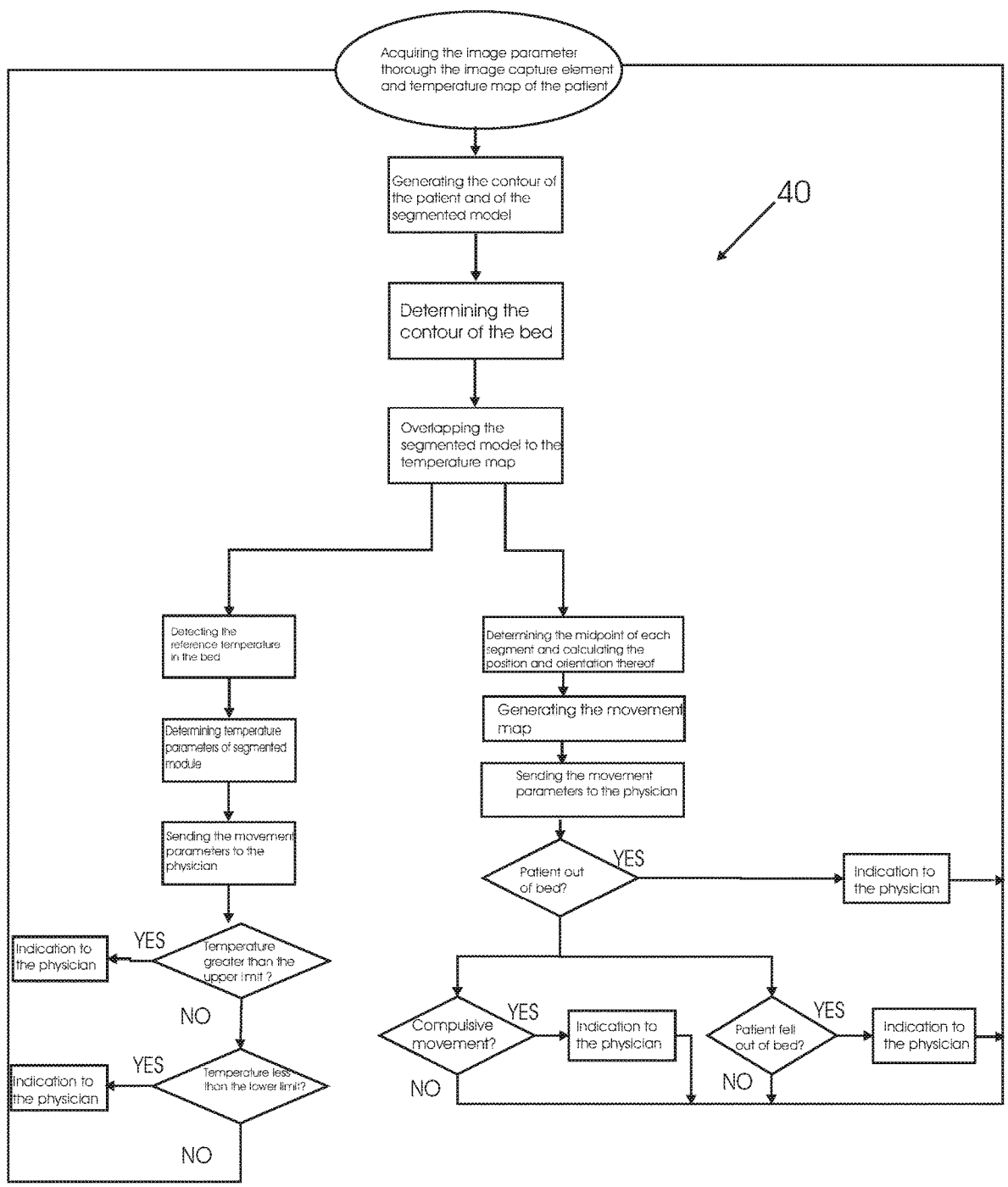
FIG. 16—illustrates a flowchart of the method for monitoring patients in hospital beds proposed in the present invention.

FIG. 16 is a preferred representation of a flowchart showing the main steps of the proposed method 40.

The proposed method 40 begins with the acquisition of the image parameter 11 through the image capture element 2 and generation of the patient's temperature map 13.

Subsequently, and in accordance with the flowchart shown in FIG. 16, the contour 14 of the patient is generated in conjunction with his/her segmented model 15.

Thereafter, and through the device 9, the contours of the hospital bed 10 are defined and, then, the overlapping of the segmented model 15 to the patient's temperature map 13 occurs.

Later on, one has the detection of the temperature parameters 16 and movement parameters 17 of patient 12.

With respect to the temperature parameters 16, a hospital bed reference temperature should preferably be set such that the temperature parameters 16 of at least one of the plurality of segments of the segmented model 15 be determined.

Thereafter, the temperature parameters 16 are sent to the health care professional, such sending, preferably, taking place for the display 4 arranged in the hospital room, to the central monitoring unit of the hospital or to the electronic device, tablet, computer) of the physician.

Next, it will be evaluated whether the temperature parameters 16 of the patient 12, or of each segment of the segmented model 15 are within the range considered to be acceptable by the healthcare professional.

If the temperature parameters 16 are above or below the predefined limits, an indication (alarm) will be sent to the health care professional.

In parallel to the determination of the temperature parameters 16, the proposed method 40 also determines the movement parameters 17 of the patient 12.

To do this, and in harmony with the system 1 previously described, one must determine the midpoint of each segment of the segmented model 15 and perform the kinematic calculation of the position and orientation thereof. Further, the movement map 27 is generated.

Subsequently, the movement parameters 17 and movement map 27 are sent to the health care professional, as well as the comparison between movement parameters 17 generated in different time instants; thus, the health care professional will be able to evaluate the movement of the patient 12 and each of the segments of the segmented model 15.

For example, and in harmony with the system 1 previously described, the health care professional can assess whether the patient 12 is out of bed, if the patient has compulsive movement or if the patient has fallen from the bed.

For any movement above the acceptable, an indication (alarm) is sent to the health care professional.

Obviously, possible evaluations of patient movement monitoring (out of bed, compulsive movement, fell from the bed) are valid for each segment of the segmented model 15.

In addition, such evaluation occurs, as already mentioned, through the determination of the midpoint M of each segment and consequent kinematic calculation of the position and orientation thereof at different time instants.

After one example of a preferred embodiment has been described, it should be understood that the scope of the present invention encompasses other possible embodiments and is limited only by the content of the appended claims, which include their possible equivalents.

The invention claimed is:

1. A system of monitoring patients in hospital beds, the system comprising:
   at least one image capture element disposed in a hospital bed and configured to generate an image parameter of a patient disposed in the hospital bed; and
   at least one processor configured to generate a temperature map of the patient from the image parameter; wherein the processor is further configured to generate, from the image parameter, a segmented model of the patient, the segmented model representing a vector illustration of the patient's body, wherein the segmented model comprises a plurality of segments, and wherein the processor is further configured to:
   determine a temperature parameter of at least one segment of the segmented model;

determine a midpoint of each segment of the segmented model;

determine a position and an orientation of each midpoint of each segment of the segmented model; and generate at least one movement parameter of the patient from the analysis of the position and of the orientation of each midpoint of each segment of the segmented model generated at different time instants.

2. The system according to claim 1, wherein the processor is configured to generate, from the image parameter, a contour of the image parameter of the patient.

3. The system according to claim 2, wherein from the segmented model of the patient, the processor is configured to indicate at least one region of a body of the patient, each region comprising at least one segment of the segmented model.

4. The system according to claim 1, wherein the processor is configured to generate a movement map with the generated segmented models, the movement map being preferably generated considering time instants defined by a user of the system.

5. The system according to claim 1, wherein the movement parameters are generated based on a kinematic calculation of the position and of the orientation of the midpoints generated at different time instants.

6. The system according to claim 5, wherein the processor is configured to indicate to a user of the system if at least one of the temperature parameters, the movement parameters, or the segmented model are outside predefined limits.

7. A method of monitoring patients in hospital beds, the hospital bed comprising at least one image capture element, such that the image capture element is associated with a processor, the method comprising the steps of:

generating an image parameter of a patient disposed in the hospital bed;

generating, thereafter, a temperature map of the patient from the generated image parameter;

wherein the method further comprises the steps of:

generating a segmented model of the patient at subsequent time instants, the segmented model representing a vector illustration of the patient's body, wherein the segmented model comprises a plurality of segments;

determining a temperature parameter of at least one segment of the segmented model;

determining a midpoint of each segment of the segmented model;

determining a position and an orientation of each midpoint of each segment of the segmented model; and generating at least one movement parameter of the patient from the analysis of the position and of the orientation of each midpoint of each segment of the segmented model generated at different time instants.

8. The method, according to claim 7, wherein it further comprises the steps of:

generating from the image parameter, a contour of the image parameter of the patient and a segmented model of the patient; and indicating, from the segmented model, at least one region of a body of the patient, each region comprising at least one segment of the segmented model.

9. The method, according to claim 8, wherein it further comprises the steps of:

generating a movement map with the generated segmented models, the movement map considering time instants defined by a user of the method of monitoring patients in hospital beds.

10. The method, according to claim 9, wherein the movement parameters are generated based on a kinematic calculation of the position and of the orientation of the midpoints generated at different time instants.

11. The method, according to claim 10, wherein it further comprises the steps of:

overlapping each segmented model with each generated temperature map; and indicating to the user of the method of monitoring patients in hospital beds at least one of the image parameters, temperature map, segmented model, movement map, temperature parameters, movement parameters of the patient, the method further comprising the step of:

indicating to the user of the method of monitoring patients in hospital beds if at least one of the temperature parameters, movement parameters and segmented model is outside predefined limits.

* * * * *